(12) United States Patent
Rochon et al.

(10) Patent No.: US 11,103,840 B2
(45) Date of Patent: Aug. 31, 2021

(54) MIXING AND DISPENSING DEVICE AND METHOD

(71) Applicant: PROCESS CLEANING SOLUTIONS LTD., Peterborough (CA)

(72) Inventors: Michael Rochon, Mansfield (CA); Asquith Williams, Bowmanville (CA)

(73) Assignee: PROCESS CLEANING SOLUTIONS LTD., Peterborough (CA)

( * ) Notice: Subject to any disclaimer, the term of this patent is extended or adjusted under 35 U.S.C. 154(b) by 99 days.

(21) Appl. No.: 16/351,976

(22) Filed: Mar. 13, 2019

(65) Prior Publication Data

US 2019/0282975 A1    Sep. 19, 2019

Related U.S. Application Data

(60) Provisional application No. 62/644,799, filed on Mar. 19, 2018.

(51) Int. Cl.
| | |
|---|---|
| *B01F 5/04* | (2006.01) |
| *B01F 3/08* | (2006.01) |
| *B01F 5/00* | (2006.01) |
| *A61L 2/18* | (2006.01) |

(52) U.S. Cl.
CPC .......... *B01F 5/0401* (2013.01); *B01F 3/0803* (2013.01); *B01F 5/0082* (2013.01); *A61L 2/18* (2013.01); *B01F 2003/0884* (2013.01); *B01F 2005/0005* (2013.01);
(Continued)

(58) Field of Classification Search
CPC .... B01F 5/0401; B01F 3/0803; B01F 5/0082;
B01F 2215/044; B01F 2005/0005; B01F 2005/0088; B01F 2215/008; B01F 2215/004; B01F 2003/0884; B01F 5/0421;
(Continued)

(56) References Cited

U.S. PATENT DOCUMENTS

| | | | | |
|---|---|---|---|---|
| 9,517,955 | B2 * | 12/2016 | Buschmann | .......... C07C 407/00 |
| 9,517,956 | B2 * | 12/2016 | Buschmann | .............. C25B 1/30 |
| 10,501,346 | B2 * | 12/2019 | Buschmann | .............. C25B 9/17 |

(Continued)

FOREIGN PATENT DOCUMENTS

| | | |
|---|---|---|
| CA | 2028930 A1 | 5/1992 |
| CN | 104 555 928 B | 3/2017 |
| WO | 2009/100870 A2 | 8/2009 |

*Primary Examiner* — Regina M Yoo
(74) *Attorney, Agent, or Firm* — Oliff PLC

(57) ABSTRACT

A mixing and dispensing device and method. In particular, the device used by the applied method reduces the risk of chlorine gas formation while providing a stable, effective and safe disinfectant in the form of a hypochlorous add and sodium hypochlorite mixture. The mixing and dispensing device includes a highly concentrated disinfectant and dilutes the concentrate through the device while simultaneously mixing the concentrate with a dilute solution of an organic acid. The two diluted solutions are mixed without production of chlorine gas and to a level of safety before being dispensed to produce the stable, effective and safe neutral pH sodium hypochlorite solution disinfectant in the form of a hypochlorous add and sodium hypochlorite mixture. The mixing and dispensing device can be in the form of a kit for retrofitting into institutions or isolated, remote areas in need thereof or for off the shelf use in the home.

10 Claims, 4 Drawing Sheets

(52) U.S. Cl.
CPC . *B01F 2005/0088* (2013.01); *B01F 2215/004* (2013.01); *B01F 2215/008* (2013.01); *B01F 2215/044* (2013.01)

(58) Field of Classification Search
CPC .......... B01F 5/0428; B01F 5/064; A61L 2/18; A61L 2202/15
See application file for complete search history.

(56) References Cited

U.S. PATENT DOCUMENTS

| | | | |
|---|---|---|---|
| 2003/0127534 A1* | 7/2003 | Firestone | B01F 15/0479 239/61 |
| 2005/0126928 A1 | 6/2005 | Hung et al. | |
| 2009/0008268 A1 | 1/2009 | Salathe et al. | |
| 2010/0307757 A1* | 12/2010 | Blow | C09K 8/605 166/308.2 |
| 2012/0228145 A1 | 9/2012 | Guastella et al. | |
| 2015/0157992 A1* | 6/2015 | Boticki | B01F 5/043 137/15.09 |
| 2016/0318778 A1* | 11/2016 | Buschmann | A01N 59/00 |
| 2019/0076009 A1* | 3/2019 | Yang | A61B 1/00057 |
| 2019/0076567 A1* | 3/2019 | Yang | A61L 2/18 |

* cited by examiner

MIXING AND DISPENSING DEVICE AND METHOD

This application claims priority from and the benefit of U.S. Provisional Application Ser. No. 62/644,799, entitled MIXING AND DISPENSING DEVICE AND METHOD filed Mar. 19, 2018, which is hereby incorporated by reference in its entirety for all purposes.

TECHNICAL FIELD OF INVENTION

A mixing and dispensing device and method. In particular, the device used by the applied method removes the risk of chlorine gas formation while providing a stable, effective and safe disinfectant in the form of a mixture having an equilibrium of almost 50% of sodium hypochlorite and hypochlorous add at a neutral pH with a much lower concentration.

BACKGROUND

The application of high concentrations of chemicals found in disinfectants used on hard, non-porous environmental surfaces in healthcare and other settings include high concentrations of chemical detergents. Major drawback with existing commercial production of disinfectants are understood to exist with the lack of stability, making the commercialization of neutral pH sodium hypochlorite products difficult. As a consequence the example of sodium hypochlorite products often do not achieve the desired level of microbial decontamination and as such routine manual cleaning of the hard, non-porous environmental surfaces in healthcare and other settings fail. Accordingly, in an effort to achieve higher levels of microbial decontamination, institutions use higher levels of microbial decontamination in the form of higher concentration levels of chemicals in an attempt to meet the challenge of ever increasing pathogen resistance in those areas of health care acquired infections. Other problems exist when such disinfectants decompose when stored for prolonged periods of time resulting in less effective disinfectants.

There is a need in the art to provide on demand a device providing a safe, stable and effective disinfectant for pathogen removal with a minimal amount of chemistry for safely cleaning, disinfecting and sanitizing environments in need thereof.

SUMMARY OF THE INVENTION

Aspects of the invention provide a mixing and dispensing device and a method for providing a stable, effective and safe disinfectant in the form of a mixture having an equilibrium of almost 50% of sodium hypochlorite and hypochlorous acid at a neutral pH with a much lower concentration without gassing-off (without producing dangerous amounts of chlorine gas). An aspect of the invention includes providing a kit of the device and components for retrofitting into areas in need thereof.

Another aspect of the device, includes an inlet in fluid communication with an adjustable valve; a connector line adjoined the adjustable valve. The connector line has a reduced diameter and in fluid communication with a horizontal line on either side of the connector line; a vertical line in fluid communication with either side of the horizontal line; an opening in each vertical line. Each opening is in fluid communication with a separate component line; a mixing area where each vertical line converge; and an outlet extending from the mixing area.

A further aspect includes, a method of mixing and dispensing a disinfectant from a device having the steps of (a) opening an adjustable valve of the device; (b) generating a flow of water through the device; (c) generating a vacuum to simultaneously draw-up separate components from source into separate vertical lines; (d) simultaneously diluting the separate components with water; (e) mixing the separate components; and (f) discharging the mixture.

The kit for mixing and dispensing a disinfectant as provided, includes a device; a first component and a second component; implementing or retrofitting the kit may optionally require instructions for using the device of the kit and the correct components; the use having the steps of (a) releasably securing the device to a main water supply; (b) releasably attaching the selected first component and the second component to the device; (c) opening the adjustable valve; and (d) discharge the dilute concentrate mixture of the first component and the second component from the outlet.

BRIEF DESCRIPTION OF THE FIGURES

The accompanying figures, which are incorporated in and constitute a part of this description, illustrate several aspects as discussed herein.

DETAILED DESCRIPTION OF THE INVENTION

The device is shown and generally designated by the numeral 5. One preferred embodiment of a mixing and dispensing device 5 is in the uniquely engineered device and method of taking a highly concentrated disinfectant, preferably a specifically formulated alkaline sodium hypochlorite solution known from the company Process Cleaning Solutions as PCS 7000 (DIN: 02314878) that is simultaneously mixed with water and a dilute solution of an organic acid, an example of such an organic acid used is acetic acid. Without the production of chlorine gas, the two separate solutions are mixed in the device before being dispensed, to form a mixture having an equilibrium of about 50% of sodium hypochlorite and hypochlorous acid at a neutral pH.

Figure 1:
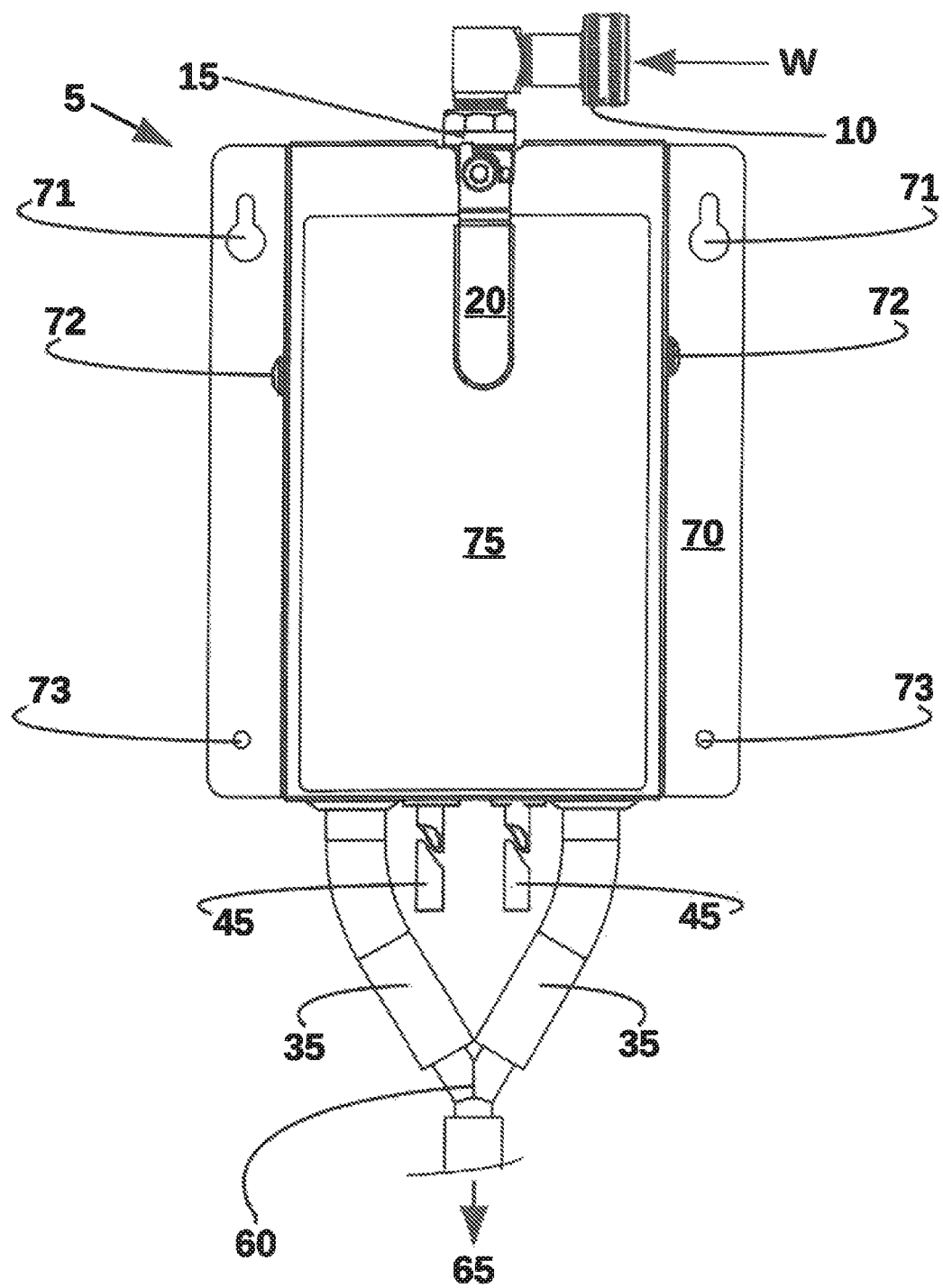
FIG. 1 is a front view with a cover plate of a device.

Referring to FIG. 1 a front view of the mixing and dispensing device 5 provided with an inlet coupling 10 for releasable attachment to a water source W. An adjustable valve 15 includes actuating handle 20 for opening and closing the valve 15. Cover plate wing 70 of cover plate 75 is used to releasably secure the device to an area of choice where a water source W exists. The cover plate 75 has an open face on to which an indicia of choice can be applied. The cover plate wing 70 integral to cover plate 75 includes openings 71 and 73 to accommodate securing means for the securing cover plate 75 and device 5 to the area of choice. Alternative means for securing the device 5 to an area of choice with a water source W may be applied according to requirements. Securing member 72 is used to releasably secure vertical line 35 to cover plate 75 via bracket 74 (shown in FIG. 2), which is integral to cover plate 75. Alternative ways of securing the guts per se of the device to an area in need thereof, are known to those of skill in the art and may be applied accordingly.

Figure 2:
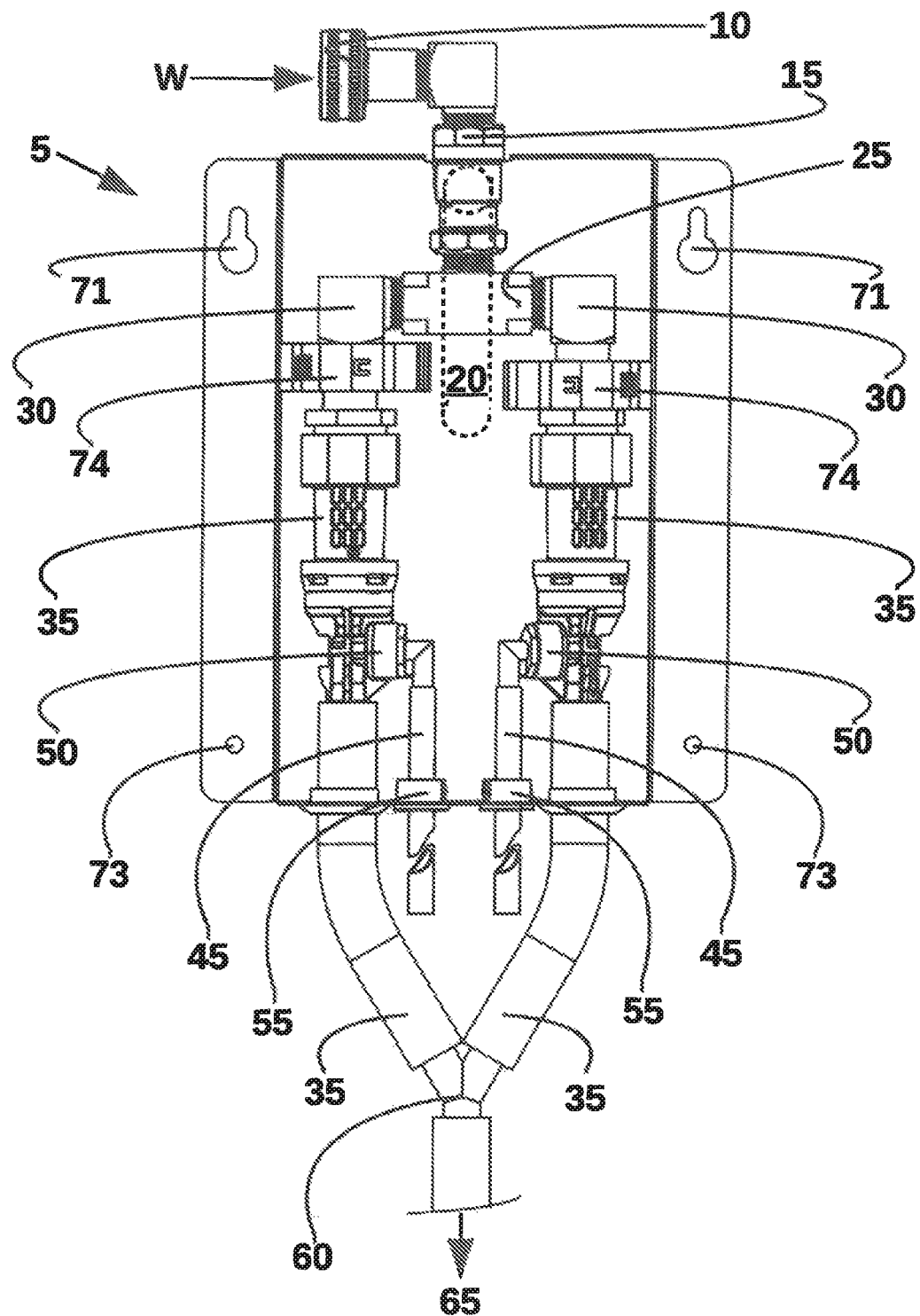
FIG. 2 is a rear view of the device in FIG. 1.

FIG. 2 is a rear view of device 5 showing the arrangement of connector line 25, horizontal line 30, vertical line 35, and the component line 45, as vertical line 35 is attached to cover plate 75 via bracket 74 the connector line 25, horizontal line 30, and the component line 45 are also held in place by each connector line 25, horizontal line 30, vertical line 35, and the component line 45 attached in fluid communication with each other. Handle 20 is shown in dotted lines indicating to provide the location at the front area of the cover plate as it relates to connector line 25, horizontal line 30 and vertical line 35. Vertical line 35 extends from horizontal line 30 all the way down to a converged mixing area 60 prior the outlet 65.

Figure 3:
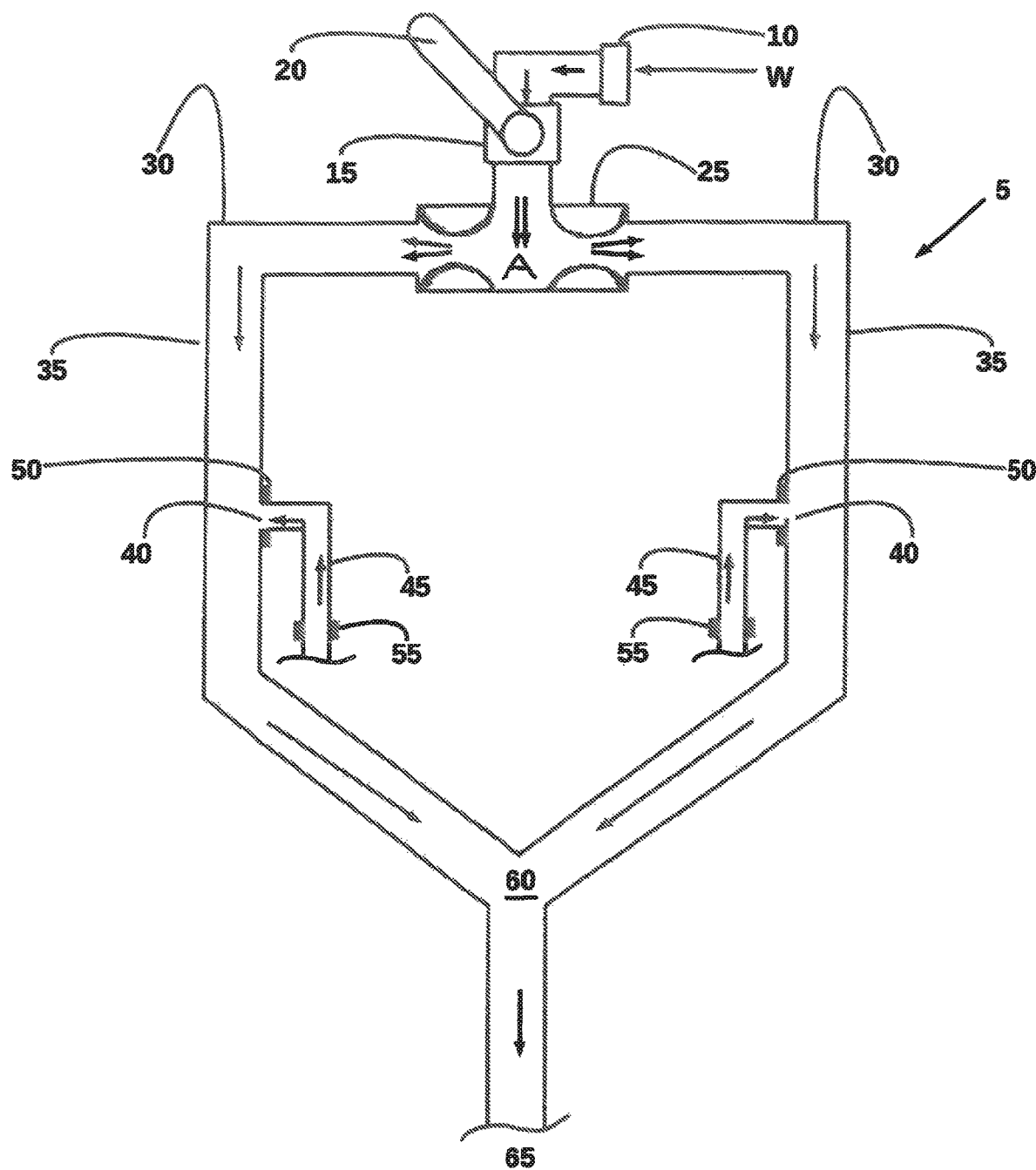
FIG. 3 is a schematic view of the device of FIG. 2.

The schematic view of FIG. 3 provides a better understanding of how the water and component flow interacts within the mixing and dispensing device 5. Accordingly inlet coupling 10 in fluid communication (indicated by the arrows) with a water source W. The water used in the device can vary from soft to hard based on the source as treated tap water to water from other sources of water W found in different environments. Adjustable valve 15 actuated with handle 20 controls water flow through device 5. Handle 20 for actuating the valve as shown in FIGS. 1, 2, 3 and 4 can vary in structure and function from a group of adjustable valves including, a rotatable valve, a stopcock, a ball valve, a push-type valve, a slider valve, and a gate valve, without departing from the required flow of water. Connector line 25 adjoined adjustable valve 15 includes area A of increase flow and reduce water pressure after the connector line and through horizontal line 30 and vertical line 35. The restricted area A of the connector line 25 may vary in shape and size without affecting the final discharged product. As water flows over opening 40 of vertical line 35 a subsequent vacuum formed in and around each opening 40 simultaneously draw-up a separate component (not shown) from line 45 into each separate vertical line 35. The horizontal line 30 and the vertical line 35 are of identical dimensions as is the component line 45. Each one of the component lines 45 are releasably engaged with a primary coupling 50 and a secondary coupling 55 engaged during instalment of the first and second components.

The strong disinfectant of the first component can have a concentration ranging from about 5,000 ppm (0.5%) to about 65,000 ppm (6.5%), whereas the second component of a weak organic acid in solution can have a concentration in the range of from about 200 ppm (0.02%) to about 65,000 ppm (6.5%). In one selected embodiment, the first component can be selected from a disinfectant cleaner, for example PCS 7000, can have a concentration in the range of about 5,000 ppm (0.5%) to about 14,000 ppm (1.4%), and the second component of a neutralizing solution, for example, PCS Neutralizing Solution, can have a concentration of about 3,500 ppm (0.35%) to about 5,000 ppm (0.5%). As the water passes over each opening 40 the subsequent vacuum produced in and around each opening 40 provide an effect to simultaneously draw-up the first component and the second component from their respective sources into the vertical lines 35 of device 5. The drawn up separate components include the first component of disinfectant in solution having a starting pH of about 11.5 to about 12.5 and the second component of a weak organic acid neutralizing solution having a starting pH of about 3.0 to about 5.0.

At step (d) the simultaneous dilution of the separate components with the incoming water adjust the pH value. For example, the pH of the second component is adjusted to not less than 4.0. In vertical line 35 at step (d) the water combines with about 7000 ppm of the first component in a ratio of 1 to 16 parts water (1:16); and simultaneously the water combines with at least 4000 ppm of the second component in a ratio of 1 to 16 parts water (1:16) at a pH of between about 4.0 to about 4.5. At the mixing step (e) the pH value of the second component is now about 9.5 to about 10.5. Slight variations can occur depending on the slight variations in pH of the water at source W.

At step (e) each vertical line 35 is converged at a mixing area 60 where the first component and the second component mix without forming harmful chlorine gas fumes also known as off-gassing. The first component and the second component are mixed at this step together with water in a ratio of 1 to 32 (1:32), the first component has a pH of between about 9.5 and about 10.5 and the second component has a pH not less than 4.0.

The safe and effective mixture is discharged from outlet 65 extending from the mixing area 60 in an equilibrium of almost 50% of sodium hypochlorite and hypochlorous acid, the mixture having a neutral pH with a much lower concentration than the first component. In an embodiment, the discharged mixture may have between about 100 ppm (0.01%) to about 5,000 ppm (0.5%) with a pH of about 7.0 to about 10.0, with an equilibrium of about 55% to 65% of sodium hypochlorite and about 25% to about 35% of hypochlorous acid in a pH of about 7.75 to about 9.5. In a select embodiment the final disinfectant in equilibrium of almost 50% of sodium hypochlorite and hypochlorous add at a neutral pH with a concentration of about 100 ppm (0.01%) to about 500 ppm (0.05%). Dependent on the required disinfectant, the application of the pH range of final product of can be varied or adjusted to accommodate those requirements, the range of pH values of the final product can include from between about 8.0 to 9.5 at the point of step (e) and beyond. An example of an end product at step (e) in equilibrium can be about 55% to 65% of sodium hypochlorite and about 25% to about 35% of hypochlorous acid in a pH of about 7.75 to about 9.5.

Figure 4:
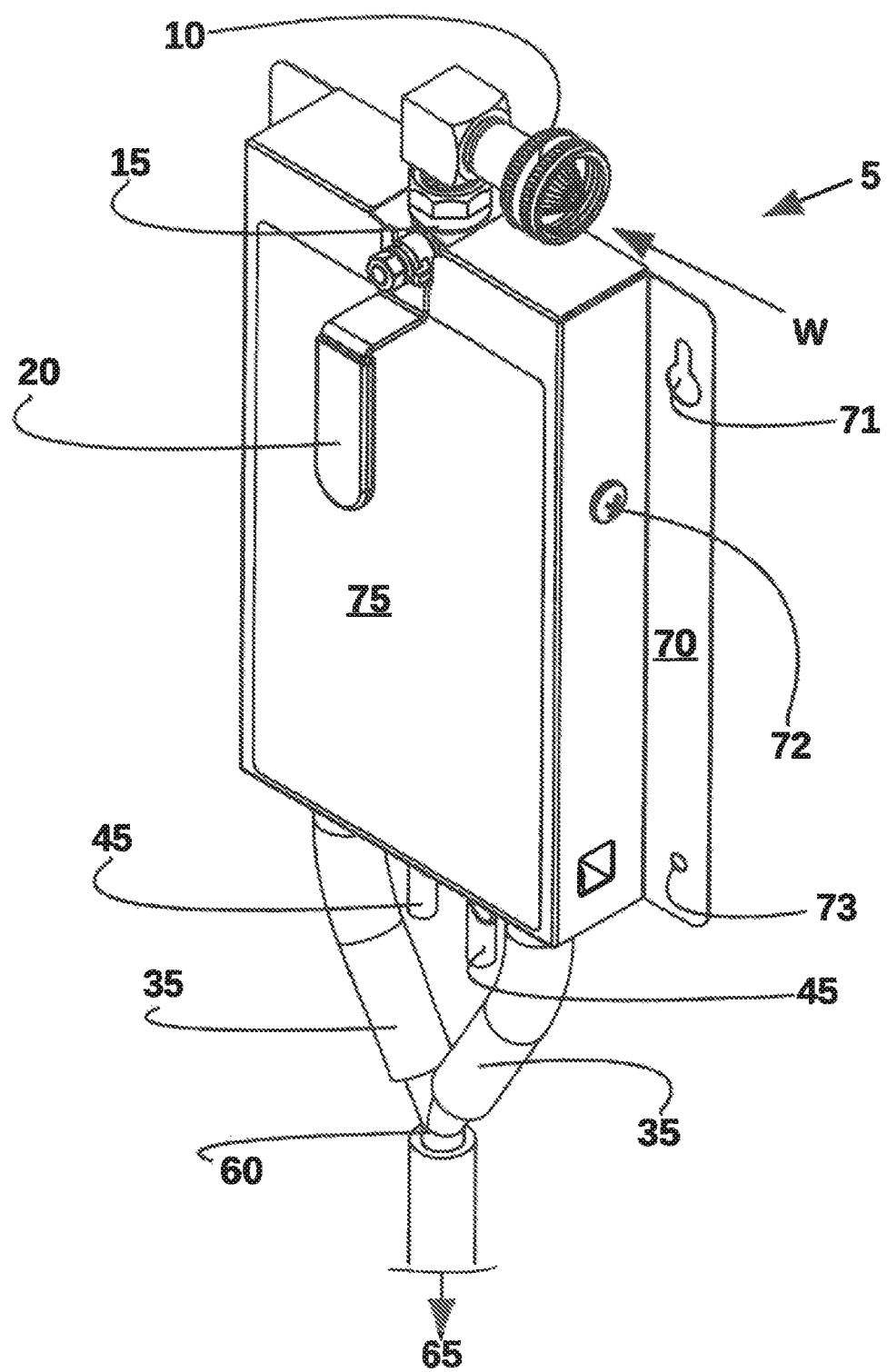
FIG. 4 is a perspective side view of the device of FIG. 1.

The connector line 25, horizontal line 30, the vertical line 35, and the component line 45 are hollow cylindrical bodies of metal, glass, plastic, rubber, or any other material used alone or in combination for conveying or transporting one or more liquids. FIG. 4 shows a perspective side view of device 5 with a cover plate wing 70 in front of the connector line 25, horizontal line 30, the vertical line 35, and the component line 45.

Retrofitting the kit of device 5 in institutions in need of on demand disinfectant, can use this disinfectant with a controlled amount of moisture, PCS micro fiber cloths following a specific wiping procedure that has shown to provide superior results compared to using the identical wiping process using same cloths, controlled moisture with saline T synthetic detergent or PCS 1000 ppm sodium hypochlorite disinfectant. It is essential to include within institutions of health, schools, and others the device 5 employing the method of mixing and dispensing an on demand disinfectant of PCS 250 Neutral pH solution from device 5 that include the steps of engaging handle 20 and opening the adjustable valve 15 of the device 5 to generating a flow of water over opening 40 which in turn instigates a pressure differential between the incoming water W and the water outlet 65 as indicated by arrows in FIGS. 1, 2, 3 and 4 through device 5. The generated vacuum simultaneously over each opening 40 draws-up separate components from source into the separate vertical lines 35 simultaneously diluting the separate components with water, in turn the separate components are mixed together and discharged.

The readily available neutral pH sodium hypochlorite solution disinfectant is stable enough to be stored and used within facilities for a prolonged period of time ranging from weeks to months while still retaining the effectiveness of the more concentrated chemically induced disinfectants. In a further select embodiment, the kit for mixing and dispensing the disinfectant is provided with the tow separate components, in that device 5 can be retrofitted into an establishment in need of the on demand disinfectant.

The kit of device 5 includes the first component and the second component with instructions for use either in loose leaf or on the front of cover plate 75 of device 5. As a retrofit kit, device 5 is releasably secured with inlet coupling 10 to a main water supply W; the first component and the second component in separate containers are releasably attached to the device via primary coupling 50 and a secondary coupling 55. The adjustable valve 15 is opened causing the first component and the second component to be drawn up from their respective containers (not shown) through the separate component line 45 and out through outlet 40 of each component line 45.

Retrofitting device 5 in kit form with existing water systems of institutions and homes in need of such device 5, is accompanied with instructions for fitting and using the device on a permanent or temporary basis. Optionally, the device 5 can be in the form of an off-the-shelf container having within one contained unit device 5 with two separate containers inside including the first component in a first container and the second component in a second container. An attachment means for releasably securing to a water source W, for example a tap, when engaged, will draw-up the two components via the created vacuum at the same time to provide the required mixing and concentration of an effective and stable disinfectant. A further option may include the use of a pump operated manually or other known means to draw-up water from a third separate container of water for use in the field of remote, isolated regions around the world in need of providing a safe, stable and effective disinfectant on demand for pathogen removal with a minimum amount of chemistry for safely cleaning, disinfecting and sanitizing of environments in need.

What is claimed is:

1. A method of mixing and dispensing a disinfectant from a device comprising the steps of:
   (a) opening an adjustable valve of the device;
   (b) generating a flow of water through the device to establish a vacuum;
   (c) drawing-up simultaneously into separate vertical lines of the device, a first component from one source and a second component from another source, wherein the first component is an alkaline sodium hypochlorite solution (PCS 7000) and the second component is a neutralizing solution of acetic acid;
   (d) diluting simultaneously the first component and the second component with the water to respectively provide a diluted first component and a diluted second component;
   (e) mixing the diluted first component and the diluted second component at a region of the device where the separate vertical lines converge into one vertical line to provide a mixture of the diluted first component and the diluted second component; and
   (f) discharging the mixture from the one vertical line.

2. The method of claim 1, wherein at step (c) the first component is a disinfectant in solution having a starting pH of about 10.0 to about 12.5 and the second component is a weak organic acid neutralizing agent in solution having a starting pH of about 2.2 to about 2.7.

3. The method of claim 2, wherein at step (c) the first component has a starting pH of 12.5 and the second component has a starting pH of 2.7.

4. The method of claim 1, wherein at step (d) the water combines with at least from about 5000 ppm (0.5%) to about 65000 ppm (6.5%) of the first component and the second component in a ratio of 1 to 16 parts water (1:16).

5. The method of claim 1, wherein at step (d) the water combines with at least 7000 ppm (0.7%) of the first component in a ratio of 1 to 16 parts water (1:16) and with at least 4000 ppm (0.4%) of the second component in a ratio of 1 to 16 parts water (1:16) at a pH of between about 3.5 to about 4.5.

6. The method of claim 1, wherein at step (e) the diluted first component has a pH of between 10.0 and 10.5 and the diluted second component has a pH not less than pH 4.0.

7. The method of claim 1, wherein at step (e) the diluted first component and the diluted second component are mixed together with water in a ratio of 1 to 32 (1:32).

8. The method of claim 1, wherein at step (f) the mixture discharged from the one vertical line is safe, stable and effective between about 100 ppm (0.01%) to about 5000 ppm (0.5%) with a pH of between 6.0 to 7.75 having an equilibrium of almost 50% of sodium hypochlorite and hypochlorous acid at a neutral pH.

9. The method of claim 1, wherein after step (f) the mixture discharged from the one vertical line is safe, stable and effective between about 10 ppm (0.01%) to about 250 ppm (0.025%) with a pH of between 8.0 to 9.5 having an equilibrium of almost 50% of sodium hypochlorite and hypochlorous acid at a neutral pH.

10. The method of claim 1, wherein after step (f) the mixture discharged from the one vertical line has an equilibrium of about 55% to about 65% of sodium hypochlorite and about 25% to about 35% of hypochlorous acid in a pH of about 7.75 to about 9.5.

* * * * *